United States Patent [19]

Lichtenthaler et al.

[11] Patent Number: 5,218,098

[45] Date of Patent: Jun. 8, 1993

[54] 5-(α-D-GLUCOPYRANOSYLOXYMETHYL)-FURAN-2-CARBOXALDEHYDE

[75] Inventors: Frieder W. Lichtenthaler, Mühltal; Dierk Martin, Dietzenbach; Thomas Weber, Birkenau; Hubert Schiweck, Worms a. Rh., all of Fed. Rep. of Germany

[73] Assignee: Sudzucker AG Mannheim/Ochsenfurt, Mannheim, Fed. Rep. of Germany

[21] Appl. No.: 606,278

[22] Filed: Oct. 31, 1990

[30] Foreign Application Priority Data

Nov. 2, 1989 [DE] Fed. Rep. of Germany ....... 3936522

[51] Int. Cl.$^5$ .......................................... C07H 15/00
[52] U.S. Cl. .................................. 536/18.5; 536/4.1; 536/17.2; 536/17.9; 536/17.7; 536/17.8; 536/53
[58] Field of Search ...................... 536/4.1, 18.5, 17.2, 536/17.9, 17.7, 17.8

[56] References Cited

PUBLICATIONS

Van Dam, H. E. et al., "The Conversion of Fructose and Glucose in Acidic Media: Formation of Hydroxymethylfurfural", Starch/Starke 38 (1986) No. 3, pp. 95-101.
Whistler, R. L. et al., Methods in Carbohydrate Chemistry. N.Y., Academic Press, 1962 pp. 316-317.

Primary Examiner—Johnnie R. Brown
Assistant Examiner—A. Varma
Attorney, Agent, or Firm—Shea & Gould

[57] ABSTRACT 5-(α-D-glucopyranosyloxymethyl)-furan-2-carboxaldehyde (GMF) is produced from isomaltulose by heating a solution of isomaltulose in a strongly polar aprotic solvent in the presence of an acidic ion-exchanger, either batchwise or by percolation of the solution through a column filled with the ion-exchanger. Novel derivatives of GMF of the formula (I)

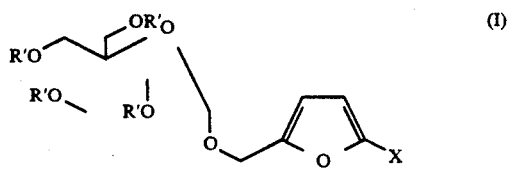

wherein R' is a hydrogen atom, an acyl group or an alkyl group and X represents —CH$_2$OH, —COOH, —C(H)=NOH, —CN, —CH$_2$NHR" or —CH=CR"R"', where R" is a hydrogen atom, an acyl or aryl group or an alkyl group with up to 20 C atoms and R"' is a hydrogen atom, —NO$_2$, —CN, —COOalkyl or acyl are described, and also their preparation and use for the preparation of surface-active compounds.

13 Claims, 3 Drawing Sheets

5-(α-D-GLUCOPYRANOSYLOXYMETHYL)-FURAN-2-CARBOXALDEHYDE

TECHNICAL FIELD OF THE INVENTION

The present invention relates to a novel process for the production of 5-(α-D-glucopyranosyloxymethyl)-furan-2-carboxaldehyde (hereinafter also called 5-glucosyloxymethylfurfural or GMF) and to derivatives and secondary products thereof of the general formula (I):

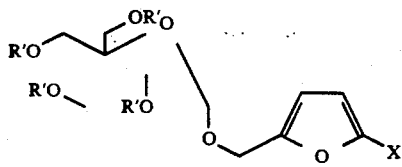

wherein R' is a hydrogen atom, an acyl group or an alkyl group and X represents —CH₂OH, —COOH, —C(H)=NOH, —CN, —CH₂NHR" or —CH=CR"R'", where R" is a hydrogen atom, an acyl or aryl group or an alkyl group with up to 20 C atoms and R'" is a hydrogen atom, —NO₂, —CN, —COOalkyl or acyl.

The acyl groups are derived from aliphatic or aromatic carboxylic acids; typical representatives are the O-acetyl and O-benzoyl derivatives.

Typical examples of alkyl groups are the methyl, ethyl and octyl groups.

SUMMARY OF THE INVENTION AND PRIOR ART

The compounds represented by the formula (I) are novel; they are technically useful, inter alia, as intermediates for chemical syntheses, for example for the preparation of surface-active compounds.

The starting material for the preparation of the compounds of the general formula (I) above is isomaltulose, i.e. the D-glucopyranosyl-α(1→6)-D-fructofuranose of formula (1) below, which undergoes a triple splitting-off of water exclusively in the fructosyl moeity on heating in polar aprotic solvents, e.g. dimethyl sulfoxide, in the presence of a weakly or strongly acidic ion-exchanger in the H+ form or of other acid catalysts. The product of this highly selective elimination of water is the 5-(α-D-glucopyranosyloxymethyl)-furan-2-carboxaldehyde of formula (2) shown in the following formula diagram:

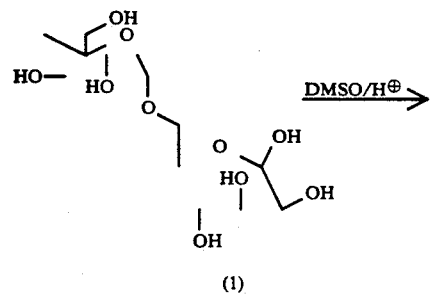

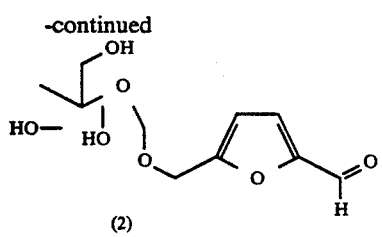

To convert the isomaltulose into the 5-glucosyloxymethylfurfural of formula (2) it is dissolved, in either anhydrous form or as monohydrate, in a strongly polar aprotic solvent, e.g. dimethyl sulfoxide, N,N-dimethylformamide, hexamethylphosphoric acid triamide (HMPT), N-methyl pyrrolidone or a mixture of these solvents, and is heated to 70°-150° C. for 0.1-24 hours in the presence of an acidic ion-exchanger, e.g. Amberlite IR-120 or Dowex 50 WX 4, each in the H+ form. The preferred conditions are heating for 4 h at 120° C. in the presence of a strongly acidic ion-exchanger (Amberlite IR-120, H+ form, dried) or for 3 h at 130° C. in the presence of Dowex 50 WX 4 (H+ form, dried); chromatographic analysis by Thin-Layer Chromatography (TLC) or High-Performance Liquid Chromatography (HPLC) shows the resulting reaction mixture to contain 65-70% GMF, 5-10% glucose and 5-hydroxymethylfurfural (HMF) (formed by glycosidic cleavage of the GMF formed), 5-10% isomaltulose dimers and 10-15% educt. While longer reaction times reduce the amount of isomaltulose remaining unchanged, they allow the contents of glucose and HMF to increase (up to 20% after 10 h), while the proportion of isomaltulose dimers remains unchanged.

Alternatively isomaltulose can be converted into mixtures of the composition given above containing 65-70% GMF by percolating a solution thereof (anhydrous or with one molecule of water of crystallisation) in dimethyl sulfoxide or other strongly polar aprotic solvents (10-100 g/100 g solvent) through a column filled with the same strongly acidic ion-exchangers at temperatures of 70°-150° C., with residence times between 20 seconds and 60 minutes. No exhaustion of the catalyst has been observed in this process.

To isolate the GMF of formula (2) that is formed, the catalyst is filtered off, the solvent is removed under vacuum and the syrup remaining is separated by elution from a silica gel or ion-exchanger column. At first dimers of the isomaltulose and isomaltulose itself are eluted, followed by GMF, which is obtained in the form of a highly viscous syrup, in yields which are throughout over 65% (cf. Example 1: 68% of theoretical). GMF can be characterised in crystalline form as 2,4-dinitrophenylhydrazone. By evaporating the last fraction to be eluted, consisting of unreacted isomaltulose and dimers thereof, to dryness under vacuum and again subjecting it to the batch process or to the continuous process in the through-flow reactor, after analogous treatment a further 15-20% GMF can be isolated, which increases the total yield to 80-85% of theoretical.

Triple splitting-off of water from ketoses to form furanoid products if known per se, as is shown by the survey by H. E. van Dam, A. P. G. Kieboom and H. van Bekkum in Stärke, 38, (1986), pp 95 ff. and the literature cited there; for example fructose can be converted in good yields to 5-hydroxymethylfurfural (HMF), inter alia by heating in aprotic solvents in the presence of acidic ion-exchangers. In practice, however, as is shown by the statements of A. Gaset et al. in FR 2 551 754 A1, a fructose:ion-exchanger ratio of 1: at least 1 is required. Using these conditions for isomatulose would lead to a considerable extent to the hydrolysis GMF→HMF. This is probably also the reason whey the selective elimination of water from ketoses combined in oligosaccharides to form the corresponding analogs of GMF was not previously known. The fact that in the case of isomaltulose this can be done selectively under relatively mild conditions, i.e. without extensive breakage of the glycosidic bonds in the molecule, is very surprising, and is inter alia the reason why an isomaltulose: ion-exchanger ratio of even 20:1 can be used in the reaction.

While the GMF of formula (2) was already mentioned in 1988 in a Japanese paper: T. Urashima, K. Suyama and S. Adachi report in *Food Chem.*, 29, 1988, pp. 7-17, on the heating of hydroxymethylfurfural and D-glucose in dioxan for 6 h at 150° C. From the resulting mixture of at least 4 chromatographically distinguishable new substances a series of syrupy products were isolated by laborious separation (preparative thin-layer chromatography) of which one was said on the basis of —C-NMR data to be the GMF of formula (2). Although the presence of GMF of formula (2) in the mixture obtained or in one of the syrupy fractions separated cannot be excluded, the proof of structure given by the Japanese authors is not conclusive, since their GMF did not crystallise. In contrast to this, we find that the GMF that we prepare from isomaltulose crystallises extremely easily from acetone or water, giving beautifully formed crystals (prisms).

By further treatment of the GMF of formula (2) or its derivatives, obtained from isomaltulose of formula (1), by reduction, oxidation, aldol-type condensation or oximation, the associated alcohol, the carboxylic acid, C-extension products or the oxime of formulae (3), (4), (9), (15) and (16) are obtained.

The O-acyl derivatives, in particular the O-acetyl and O-benzoyl derivatives, of the above-mentioned glucosyloxymethylfurfural and its derivatives can be obtained by treatment of the respective non-O-acylated starting compounds with acylating agents in anhydrous organic solvents.

BRIEF DESCRIPTION OF THE DRAWINGS

In the accompanying drawings.

DESCRIPTION OF PREFERRED EMBODIMENTS OF THE INVENTION

The formation of derivatives, e.g. the tetraacetate, of the glucosyloxymethylfurfural (GMF, formula 2), can be carried out straightforwardly under the usual conditions (acetic anhydride/pyridine) (cf. Example 2). Similarly the reduction of the aldehyde group of the GMF to the 2-glucosyloxymethyl-5-hydroxymethylfuran of formula (3) takes place smoothly using a whole series of different processes: hydride addition by treatment with sodium borohydride in methanol or pressure hydrogenation using a Cu/Cr catalyst at 140° C./100 bar, or a crossed Cannizaro reaction on treatment with formaldehyde in caustic soda.

The selective oxidation of the aldehyde group of the GMF to a carboxylic acid group takes place on treatment with sodium chlorite in an aqueous solution buffered with potassium hydrogen phosphate without any adverse effect on the four hydroxyl groups in the glycosyl moeity. The free chlorine formed is taken up with sulfamic acid. The reaction proceeds rapidly, is already complete at the end of the addition of oxidant, and gives the 5-glucosyloxymethylfuran-2-carboxylic acid of formula (4) in 80% yield.

The GMF carboxylic acid of formula (4) can be smoothly esterified, as is shown by the preparation of the methyl (formula 5), ethyl (formula 6) and octyl (formula 7) esters (cf. Examples 5-7). Furthermore the methyl ester can be converted smoothly by ammonolysis to the beautifully crystalline GMF carbonamide of the formula (8).

The GMF oxime of formula (9) is formed by treatment of GMF with hydroxylammonium chloride/sodium acetate in aqueous-ethanolic solution and separates as beautifully formed crystals in 71% yield. Treatment of the GMF oxime of formula (9) with acetic anhydride leads first of all to the penta-O-acetyl compound, which under severer conditions (heating) splits off acetic acid and goes smoothly over (78%) to the nitrile of formula (14). Hydrogenation with Raney nickel in acetic acid gives the corresponding amine, which was characterised in crystalline form as N-acetate. The free amine of formula (10) an be obtained direct from GMF by reductive amination by subjecting GMF to hydrogenation under pressure (150 bar) in methanolic ammonia with Raney nickel. Using primary amines, e.g. methylamine or dodecylamine, instead of ammonia gives the corresponding N-alkylamino compounds of formula (12) in yields that generally exceed 80%.

The aldehyde group of the GMF readily undergoes further reactions of the aldol condensation type to form the corresponding carbonyl olefination products; thus on treatment of GMF with acetophenone in the presence of NaOH the benzoylvinyl substituted derivative of formula (15), or on treatment with malodinitrile the dicyanovinyl analog of formula (16), are smoothly formed.

Figure 2A:
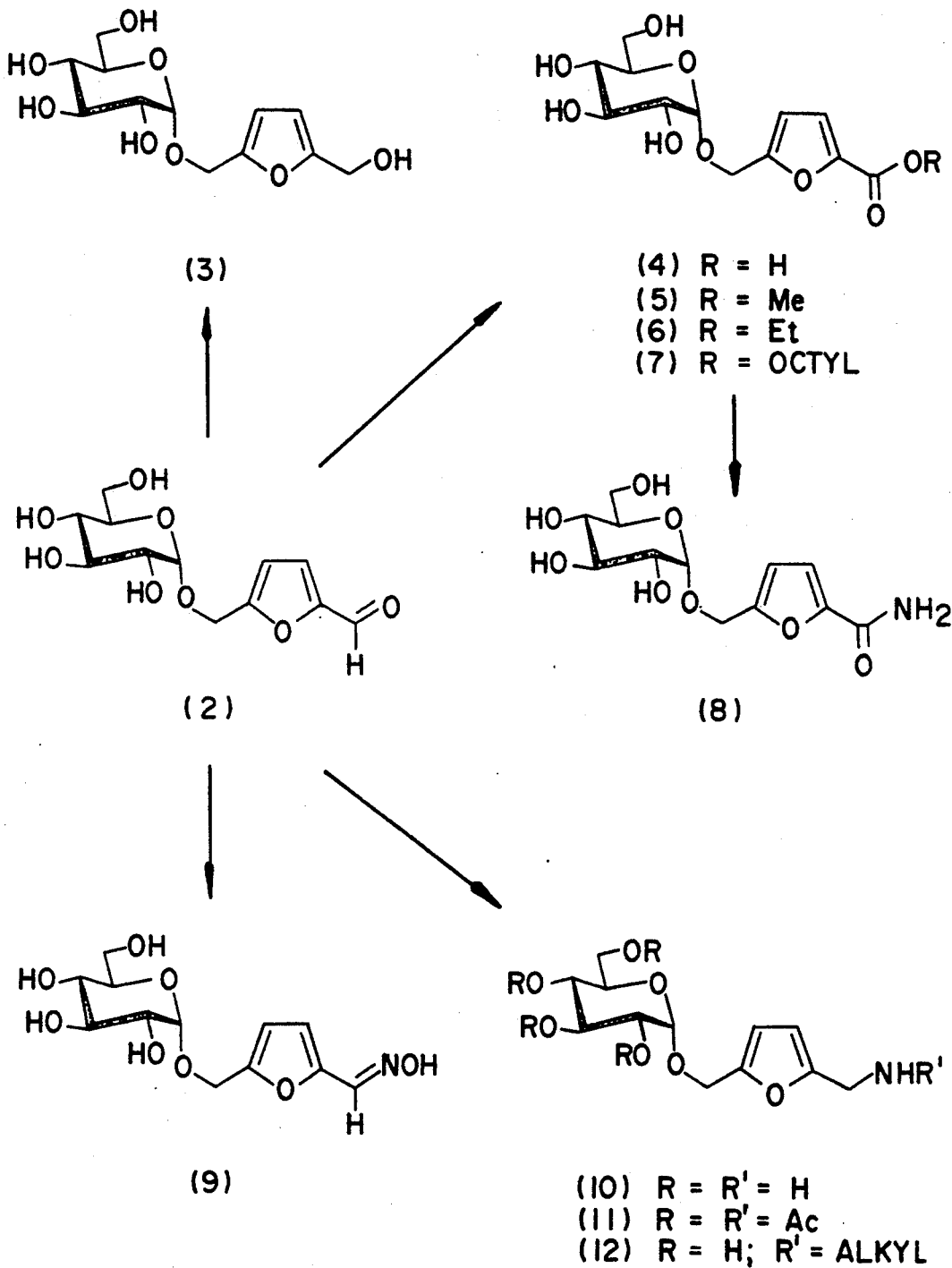
FIGS. 2a and 2b are diagrams showing the course of the above-mentioned reactions of GMF and the formulae of some of the products obtained.
Figure 2B:
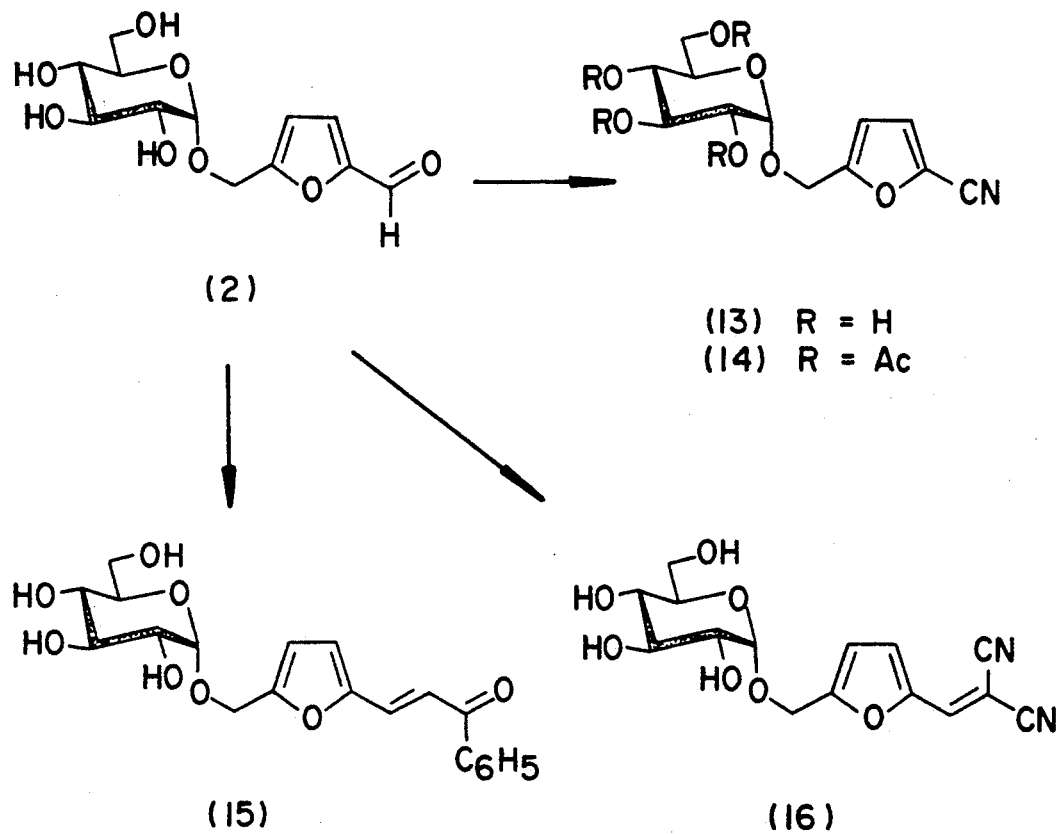

All the compounds prepared for the first time and shown in the diagram of FIG. 2, that is to say, the products having the formulae (3) to (16), have been clearly characterised microanalytically and chromatographically as pure substances; their constitution and configuration have been proved beyond doubt by 300 MHz-$^1$H-NMR spectra and using $^{13}$C-NMR and mass-spectroscopic data.

Some examples illustrating the invention will now be given.

EXAMPLE 1

5-($\alpha$-D-glucopyranosyloxymethyl)-furan-2-carboxaldehyde (formula 2): 5-$\alpha$-D-glucosyloxymethylfurfural, GMF)

Method A

A solution of 90 g (0.25 mol) isomaltulose monohydrate (formula 1) in 900 ml dimethyl sulfoxide was heated to 120° C. in a 1.5 l round-bottomed flask. 10 g of a strongly acidic ion-exchanger (Amberlite IR 120, H+ form, dried in vacuum over $P_2O_5$ for 24 h) was added and the mixture maintained at 120° C. for 4 h with stirring. According to TLC [mobile solvent acetonitrile/- water (4:1); $R_f$ values: 0.10 (dimers of isomaltulose), 0.15 (osomaltulose), 0.26 (glucose), 0.48 (GMF), 0.61 (HMF)] and HPLC the mixture consisted of 65–70% GMF, ca. 10% isomaltulose dimers, 5–10% HMF+glucose and ca. 10% educt. For working up the ion-exchanger was filtered off and the solvent removed under vacuum at 80° C. bath temperature. The brown syrup remaining was dissolved in water (250 ml), added to a Lewatit TSW 40 column ($Ca^{2+}$ form, 8×200 cm) that had been preheated to 60° C., and eluted with water (10 l/hr). The first fraction (2 l), which appeared after a ca. 3 l preflow of water, contained the dimers of the isomaltulose and unreacted isomaltulose (for further treatment of this fraction vide infra); glucose was then eluted, followed by GMF (ca. 6 l). Concentration of the GMF-containing eluate gave 49 g (68% of the theoretical) of a chromatographically and $^1$H-NMR spectroscopically homogeneous viscous syrup with $[\alpha]_D^{20} = +125°$ (c=1.3, methanol), which can be used directly for secondary reactions.

Purification of the crude product by elution from a silica gel column (3×30 cm for 5 g syrup) with acetone and concentration of the eluate gave first of all yellowish crystals of m.p. 88°–89° C.; after two recrystallisations the GMF was obtained in the form of beautifully-formed colourless prisms of m.p. 96° C. and $[\alpha]_D^{20} = +131°$ (c=1, methanol).

$^1$H-NMR (300 MHz, DMSO-$d_5$): $\delta = 3.12$ (m, 1 H, 4'-H), 3.25 (m, 1H, 2'-H), 3.38–3.64 (m, 4 H, 3'-H, 5'-H, 6'-$H_2$), 4.54 (t, 1 H, 6'-OH), 4.56 (d, 1 H, 7-$H_a$), 4.69 (d, 1 H, 7-$H_b$), 4.80 (d, 1 H, 1'-H), 4.84 (d, 1 H, OH), 4.87 (d, 1 H, OH), 4.95 (d, 1 H, OH), 6.77 (d, 1 H, 4 H), 7.53 (d, 1 H, 3-H), 9.59 (s, 1 H, CHO); $J_{3,4}=3.3$, $J_{7a,7b}=13.5$, $J_{1',2'}=3.3$, $J_{6',6'\text{-}OH}=6.2$ Hz.

—C-NMR (75.5 MHz, DMSO-$d_6$): $\delta = 60.5$ (C-7), 60.8 (C-6'), 70.1 (C-4'), 71.8 (C-2'), 73.1 (C-3', C-5'), 98.4 (C-1'), 112.0 (C-4), 124.2 (C-3), 152.2 (C-5), 158.0 (C-2), 178.3 (C-6).

MS (FD): m/e=288 ($M^+$), 289 ($M^+$ +1).

$C_{12}H_{16}O_8$ (288.25): Calc. C, 50.00; H, 5.60,

Found C, 49,81; H, 5.63,

Evaporating the first fraction consisting of isomaltulose and its dimers (see above) to dryness and subjecting the residue, in solution in DMSO, to the reaction conditions set out above, gave after chromatographic separation a further 11 g (15% of theoretical) GMF (total yield 80%). It is however more practical preparatively to mix this solution containing isomaltulose and its dimers with the material fed into the through-flow reactor of FIG. 1.

Method B

Figure 1:
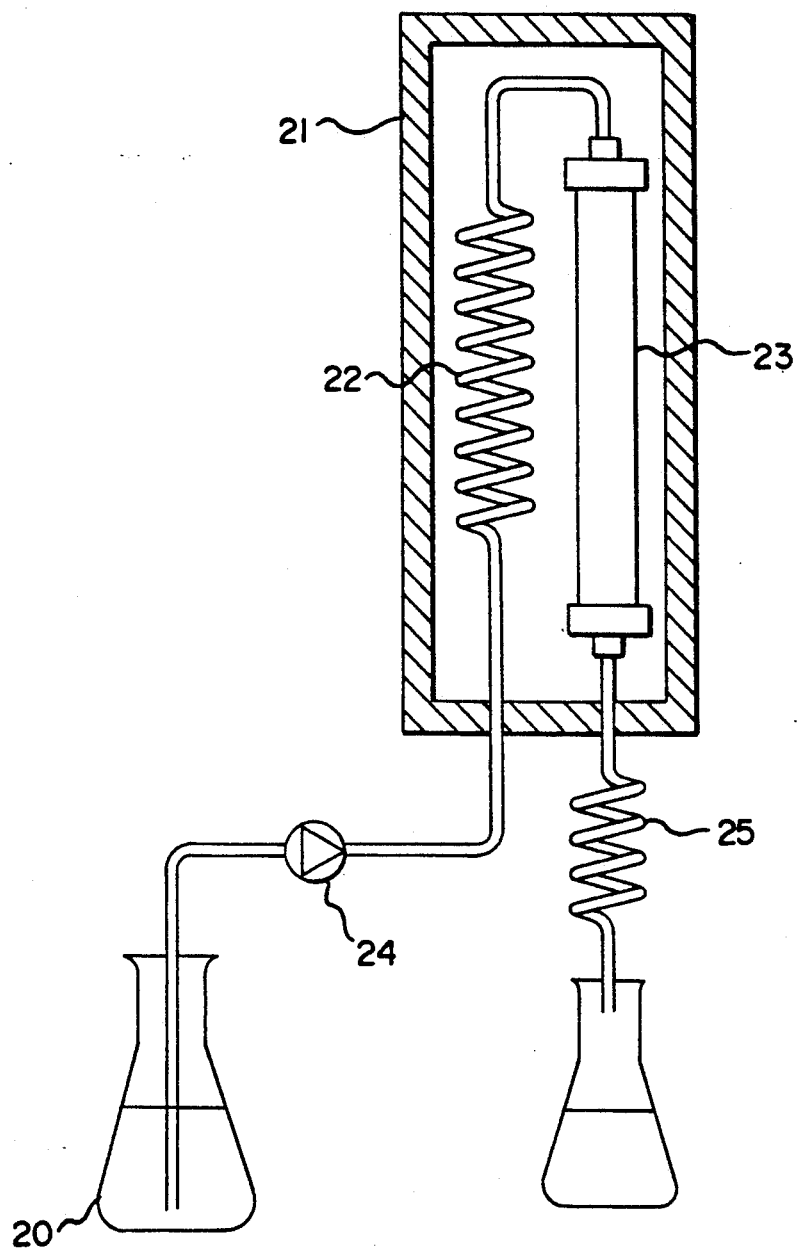
FIG. 1 is a diagram of a through-flow reactor that may be used for the conversion of isomaltulose into GMF.

In the apparatus shown in FIG. 1, a solution of 250 g isomaltulose monohydrate in 1 l DMSO from a supply vessel 20 was pumped by a pump 24 via a coil 22 in which it was heated to 130° C. through a 1.6×25 cm column 23 filled with strongly acidic ion-exchanger of the Dowex 50 XW 4 type (in H+ form) at a flow rate such that the residence time of the solution in contact with the ion-exchanger did not exceed 4 minutes. The preheating coil 22 and the reactor column 23 were enclosed in a reaction chamber 21, which may be an oven. After leaving the reaction chamber the reaction mixture was cooled in a cooling coil 25. Separation of the reaction mixture, which had a composition substantially analogous to the mixture obtained in the batch process described above, was carried out as in Method A, and gave 138 g (69% of theoretical) GMF of formula (2).

GMF dinitrophenylhydrazone: A solution of 5.0 g (25 mmol) of 2,4-dinitrophenylhydrazine in 25 ml conc. sulfuric acid was carefully diluted with 60 ml water and 200 ml ethanol, and 2.9 g (10 mmol) GMF, dissolved in 25 ml ethanol, was added to the still hot solution. After 24 h the deep red precipitate was filtered off, washed with water and recrystallised from ethyl acetate: 2.5 g (54%) of orange crystals; m.p. 186° C., $[\alpha]_D^{20} = +80.8°$ (c=1, dimethyl sulfoxide).

$^1$H-NMR (300 MHz, DMSO-$d_6$): $\delta = 3.15$ (dd, 1 H, 4'-H), 3.25 (dd, 1 H, 2'-H), 3.4–3.7 (m, 4 H, 3'-H, 5'-H, 6'-$H_2$), 4.7 (m, 4 H, 2'-OH, 3'-OH, 4'-OH, 6'-OH), 4.66 (d, 1 H, 7-$H_a$), 4.78 (d, 1 H, 7-$H_b$), 4.86 (d, 1 H, 1'-H), 6.78 (d, 1 H, 4-H), 7.11 (d, 1 H, 3-H), 7.61 (s, 1 H, 6-H), 7.96 (d, 1 H, 6''-H), 8.37 (dd, 1 H, 5''-H), 8.83 (d, 1 H, 3''-H), 12.72 (s, 1 H, N-H); $J_{3,4}=3.5$, $J_{7a,7b}=13.6$, $J_{1',2'}=3.6$, $J_{2',3'}=9.7$, $J_{3',4'}=9.0$, $J_{4',5'}=9.2$, $J_{3'',5''}2.5$, $J_{5'',6''}=9.6$ Hz.

—C-NMR (75.5 MHz, DMSO-$d_6$): $\delta = 60.5$ (C-6'), 60.9 (C-7), 69.8 (C-4'), 71.6 (C-2'), 72.9, 73.0 (2 C, C-5', C-3'), 98.7 (C-1'), 111.5 (C-4), 116.0 (C-6''), 118.7 (C-3), 122.7 (C-3''), 129.6, 137.5, 144.4 (3 C, C-1'', C-2'', C-4''), 130.0 (C-5''), 131.5 (C-6), 147.0 (C-5), 155.2 (C-2).

$C_{18}H_{20}N_4O_{11}$ (468.4): Calc. C, 46.16; H, 4.30; N, 11.96.

Found C, 46.23; H, 4.29; N, 11.84.

Method C:

A double-walled steel column (2.5×80 cm) was filled with ca. 400 ml of a catalyst resin, e.g. of the K 2411 (Bayer) type in the H+ form, pre-swollen in DMSO, and closed by means of perforated plates.

The column was heated to 90° C. through the jacket by means of a circulation thermostat and a tempering liquid.

A solution of 9 kg isomaltulose monohydrate in 9 kg DMSO was passed through the catalyst resin by means of a pump, the flow rate being such that the residence time of the solution in the catalytic reactor was about 30 minutes. The content of GMF in the eluate amounted to 50–60% of the dry substance.

The reaction mixture was substantially completely freed from solvent under high vacuum at a bath temperature of 80°–90° C. The residue was diluted with the same volume of water and chromatographically separated through a Lewatit TSW 40 column ($Ca^{++}$ form, dimensions 0.25×12 m) at 65° C.

The GMF-containing fractions were evaporated to a dry substance content of 80–85%.

By slow cooling of the aqueous solution from 70° C. at a cooling rate of 1 K·$h^{-1}$, GMF crystals having a purity of ca. 97% (HPLC) were obtained.

The yield amounted to 2.1 kg (29%, based on the isomaltulose monohydrate used).

Further product could be recovered from the mother liquor.

By recrystallisation under the same conditions GMF with a purity of 100% (HPLC) was obtained.

M.p. 88° C; $[\alpha]_D^{20} = +98°$ (c=1, $H_2O$); +131° (c=1, methanol).

EXAMPLE 2

5-(2',3',4',6'-tetra-O-acetyl-α-D-glucopyranosyloxymethyl)-furan-2-carboxaldehyde (GMF tetraacetate)

0.3 ml acetic anhydride was added at 0° C. to a solution of 60 mg (0.3 mmol) glucosyloxymethylfurfural (formula 2, product of Example 1) in 25 ml pyridine. After warming the ingredients to room temperature and further stirring during 2 h, hydrolysis was performed with ice water. By taking up the reaction solution in chloroform, washing neutral with 2N sulfuric acid, saturated sodium carbonate solution and water, drying over magnesium sulfate and removal of the solvent, 98 mg (84%) GMF tetraacetate was obtained as syrup with $[\alpha]_D^{20} = +132.8°$ (c=2.7, chloroform).

$^1$H-NMR (300 MHz, CDCl$_3$): $\delta = 1.94, 1.96, 1.97, 2.02$ (4 s, je 3 H, 4 Ac-CH$_3$), 3.99 (m, 2 H, 5'-H, 6'-H$_a$), 4.19 (dd, 1 H, 6'-H$_b$), 4.57 (d, 1H, 7-H$_a$), 4.66 (d, 1 H, 7-H$_b$), 4.79 (dd, 1 H, 2'-H), 5.01 (dd, 1 H, 4'-H), 5.13 (d, 1 H, 1'-H), 5.41 (dd, 1 H, 3'-H), 6.50 (d, 1 H, 4-H), 7.16 (d, 1 H, 3-H), 9.56 (s, 1 H, CHO); $J_{3,4}=3.5$, $J_{7a,7b}=13.5$, $J_{1',2'}=3.8$, $J_{2',3'}=10.3$, $J_{3',4'}=9.7$, $J_{4',5'}=9.6$, $J_{5',6'}=4.8$, $J_{6a,6b}=12.9$ Hz.

$^{13}$C-NMR (75.5 MHz, CDCl$_3$): $\delta = 20.5, 20.6, 20.7,$ (4 C, Ac-CH$_3$), 61.6 (C-6'), 62.0 (C-7), 67.7 (C-5'), 68.3 (C-4'), 69.8 (C-3'), 70.6 (C-2'), 95.4 (C-1'), 112.1 (C-4), 121.9 (C-3), 152.9, 156.2 (2 C, C-5, C-2), 169.5, 170.0, 170.5 (4 C, 4 Ac-C=0), 177.6 (C-6).

MS (FD): m/e=456 (M+), 457 (M+ +1).

EXAMPLE 3

2-(α-D-glucopyranosyloxymethyl)-5-hydroxymethyl-furan (formula 3)

520 mg (1.8 mmol) glucosyloxymethylfurfural (formula 2, product of Example 1) was dissolved in 30 ml methanol, and 138 mg (3.6 mmol) sodium borohydride added. After stirring for 2 h at room temperature the thin-layer chromatogram showed no further educt. To work up the product, the solvent was removed under vacuum and the syrup remaining purified by elution with chloroform/methanol (3:1). After evaporation of the fractions 443 mg (85%) glucosyloxymethylhydroxymethylfuran of formula (3) remained as a colourless syrup with $[\alpha]_D^{20} = +107°$ (c=1, methanol).

$^1$H-NMR (300 MHz, CDCl$_3$): $\delta = 3.13$ (dd, 1 H, 4'-H), 3.27 (dd, 1 H, 2'-H), 3.41–3.70 (m, 4 H, 3'-H, 5'-H, 6'-H$_2$), 4.41 (d, 1 H, 7-H$_a$), 4.41 (s, 2 H, 6-H$_2$), 4.59 (d, 1 H, 7-H$_b$), 4.79 (d, 1 H, 1'-H), 5.2 (m, 5 H, 6-OH, 2'-OH, 3'-OH, 4'-OH, 6'-OH), 6.28 (d, 1 H, 4-H), 6.40 (d, 1 H, 3-H): $J_{3,4}=2.8$, $J_{7a,7b}=12.8$, $J_{1',2'}=3.3$, $J_{2',3'}=9.6$, $J_{3',4'}=9.0$, $J_{4',5'}=9.0$ Hz.

$^{13}$C-NMR (75.5 MHz, CDCl$_3$): $\delta = 56.1, 60.6, 61.3$ (3 C, C-6, C-7, C-6'), 70.7, 72.2, 73.2, 73.6 (4 C, C-2', C-3', C-4', C-5'), 99.1 (C-1'), 107.9 (C-4), 110.5 (C-3), 150.9 (C-2), 156.0 (C-5).

MS (FD): m/e=290 (M+).

EXAMPLE 4

5-(α-D-glucopyranosyloxymethyl)-furan-2-carboxylic acid (formula 4)

3.16 g (11 mmol) GMF (formula 2, product of Example 1) and 2.13 g (22 mmol) sulfamic acid were dissolved in 50 ml water. To this 20 ml of an aqueous solution of 1.0 g (11 mmol) sodium chlorite and 1.1 g (8.1 mmol) potassium hydrogen phosphate was added dropwise during 20 min. After addition of the oxidant solution the chromatogram showed complete reaction. The solvent was removed under vacuum and the remaining syrup taken up in a mixture of 40 ml methanol and 40 ml ethanol. The inorganic salts precipitated were filtered off and the solvent again removed. Filtration of the residue through a silica gel column with methanol/chloroform (2:1) and evaporation of the eluate gave 2.9 g (89%) of carboxylic acid of formula (4) as a solid that has not yet crystallized.

Alternatively 1.6 ml (4.0 mmol) 10% NaOH were added dropwise with stirring to a solution of 0.6 g (3.5 mmol) silver nitrate in 10 ml water. The silver oxide precipitated was filtered off, washed free of nitrate with 100 ml water, and transferred while still moist to a flask in which it was suspended in 15 ml water that contained 0.7 ml (1.7 mmol) 10% NaOH. To this suspension 0.5 g (1.7 mmol) GMF was added with vigorous stirring, whereupon a colour change from brown to black and a temperature increase to 30° C. were observed. After 15 min (TLC monitoring with mobile solvent acetone/water (4:1), R$_f$(product)=0.22) silver was filtered off, the filtrate neutralised with acid ion-exchanger (Amberlite IR-120, H+ form) and evaporated down under vacuum. The resulting colourless syrup was purified on a silica gel column (3×20 cm) by elution with chloroform/methanol (2:3). The result was 460 mg (89%) of chromatographically and $^1$H-NMR spectroscopically homogeneous, amorphous solid with $[\alpha]_D^{20} = +104°$ (c=0.7, methanol).

$^1$H-NMR (300 MHz, DMSO-d$_6$): $\delta = 3.06$ (dd, 1 H, 4'-H), 3.19 (dd, 1 H, 2'-H), 3.41 (m, 4 H, 3'-H, 5'-H, 6'-H$_2$), 3.63 (d, 1 H, OH), 4.18 (m, 1 H, OH), 4.38 (d, 1 H, 7-H$_a$), 4.53 (d, 1H, 7-H$_b$), 4.74 (d, 1 H, 1'-H), 4.99 (m, 1 H, OH), 5.16 (m, 1 H, OH), 6.38 (d, 1 H, 4-H), 6.65 (d, 1 H, 3-H); $J_{3,4}=3.5$, $J_{7a,7b}=12.8$, $J_{1',2'}=3.6$, $J_{2',3'}=9.4$, $J_{3',4'}=9.2$ Hz.

$^{13}$C-NMR (75.5 MHz, DMSO-d$_6$): $\delta = 60.6$ (C-7), 61.0 (C-6'), 70.4 (C-4'), 72.0 (C-2'), 73.2 (C-3', C5'), 98.2 (C-1'), 111.4 (C-4), 116.7 (C-3), 145.5 (C-5), 154.2 (C-2), 161.0 (C-6).

MS (FD, 10–15 mA): m/e=305 (M+ +1), 327 (M+ +Na).

C$_{12}$H$_{16}$O$_9$ (304.25): Calc. C, 47.37; H, 5.30.
Found C, 47.30; H, 5.27.

EXAMPLE 5

5-(α-D-glucopyranosyloxymethyl)-furan-2-carboxylic acid methyl ester (formula 5)

To produce diazomethane, 1.0 g (10 mmol) N-methyl-N-nitrosourea was added portionwise with cooling to 20 ml diethyl ether to which 7 ml of 40% KOH had been added to form a lower layer, in such a way that the reaction temperature did not exceed +5° C. 30 min after the last addition the yellow organic phase was separated off and allowed to stand for 3 h over a little solid KOH. Enough of the ethereal solution of diazomethane thus obtained was added at room temperature with stirring during a period of 15 min to a solution of 500 mg (1.6 mmol) GMF carboxylic acid (formula 4, product of Example 4) in 18 ml methanol and 2 ml water for the yellow colour just to remain and no further evolution of gas to be observed. After a further 15 min stirring the reaction was complete (TLC monitoring with mobile solvent chloroform/methanol (2:1), R$_f$ (educt)=0, R$_f$(product)=0.41), whereupon the solvent was removed under vacuum and the crude product was purified by elution from a silica gel column (3×20 cm) with chloroform/methanol (2:1). Concentration of the fractions containing the product gave 440 mg (84%) of colourless syrup with $[\alpha]_D^{20} = +113°$ (c=0.8, methanol), which gradually crystallised on scratching; m.p. 72° C.

$^1$H-NMR (300 MHz, D$_2$O) $\delta = 3.44$ (dd, 1 H, 4'-H, 3.57 (dd, 1 H, 2'-H), 3.66 (ddd, 1 H, 5'-H), 3.71 (dd, 1 H, 3'-H), 3.75 (d, 2 H, 6'-H$_2$), 3.91 (s, 3 H, OCH$_3$), 4.73 (s, 2 H, 7-H$_2$), 5.05 (d, 1 H, 1'-H), 6.67 (d, 1 H, 4H), 7.29 (d, 1 H, 3-H); $J_{3,4}=3.5$, $J_{1',2'}=3.7$, $J_{2',3'}=9.8$, $J_{3',4'}=9.3$, $J_{4',5'}=10.0$, $J_{5',6'}=3.6$ Hz.

MS (FD, 0-15 mA): m/e=318 (M+).

$C_{13}H_{18}O_9$ (318.28): Calc. C, 49.06; H, 5.70.
Found C, 48.72; H, 5.65.

EXAMPLE 6

5-(α-D-glucopyranosyloxymethyl)-furan-2-carboxylic acid ethyl ester (formula 6)

To a solution of 300 mg (1 mmol) GMF carboxylic acid of formula (4), 0.6 g (13.0 mmol) ethanol and 20 mg p-toluenesulfonic acid in 3 ml pyridine was added 200 mg (1.0 mmol) dicyclohexylcarbodiimide, and the mixture was stirred at room temperature for 24 h. After filtration it was completely concentrated under vacuum, repeatedly reevaporated with toluene, and the resulting syrup was purified through a silica gel column (3×20 cm) by elution with chloroform/methanol (7:2). Evaporation of the fractions with $R_f=0.31$ gave 190 mg (60%) of ethyl ester of the formula (6) as a colourless syrup, with $[α]_D^{20}=+108°$ C. (c=0.7, methanol).

$^1$H-NMR (300 MHz, D$_2$O): δ=1.37 (t, 3H, OCH$_2$CH$_3$), 3.44 (dd, 1 H, 4'-H), 3.56 (dd, 1 H, 2'-H), 3.65 (ddd, 1 H, 5'-H), 3.70 (dd, 1 H, 3'-H), 3.75 (d, 2 H, 6'-H$_2$), 4.38 (q, 2H, OCH$_2$CH$_3$), 4.73 (s, 2 H, 7-H$_2$), 5.04 (d, 1 H, 1'-H), 6.67 (d, 1 H, 4-H), 7.30 (d, 1 H, 3-H); $J_{3,4}=3.5$, $J_{8,9}=7.1$, $J_{1',2'}=3.8$, $J_{2',3'}=9.8$, $J_{3',4'}=9.3$, $J_{4',5'}=10.2$, $J_{5',6'}=3.6$ Hz.

MS (FD, 0-12 mA): m/e=332 (M+).

$C_{14}H_{20}O_9$ (332.31): Calc. C, 50.60; H, 6.07.
Found C, 49.91; H, 6.31.

EXAMPLE 7

5-(α-D-glucopyranosyloxymethyl)-furan-2-carboxylic acid octyl ester (formula 7)

Replacing ethanol in the previous example by the equivalent amount of 1-octanol gave the corresponding octyl ester of formula (7) after chromatographic purification (elution with chloroform/methanol (7:2)) in the form of a white amorphous powder; $[α]_D^{20}=+86°$ (c=0.7, methanol).

$^1$H-NMR (300 MHz, DMSO-d$_6$): δ=0.86 (t, 3 H, CH$_3$), 1.03-1.77 (m, 12 H, [CH$_2$]$_6$), 3.09 (m, 1 H, 2'-H), 3.23 (m, 1 H, 4'-H), 3.34-3.64 (m, 4 H, 3'-H, 5'-H, 6'-H$_2$), 4.23 (t, 2 H, OCH$_3$), 4.48 (m, 1 H, OH), 4.52 (d, 1 H, 7 H$_a$), 4.64 (d, 1 H, 7-H$_b$), 4.75-4.82 (m, 3 H, 1'-H, 2 OH), 4.90 (d, 1 H, OH), 6.56 (d, 1 H, 4-H), 6.87 (d, 1 H, 1'-H); $J_{3,4}=3.4$, $J_{7a,7b}=13.4$, $J_{8,9}=6.7$, $J_{14,15}=6.7$, $J_{1',2'}=3.6$ Hz.

MS (FD, 0-20 mA): m/e=416 (M+), 417 (M+ +1).

$C_{20}H_{32}O_9$ (416.47): Calc. C, 57.68; H, 7.74.
Found C, 56.75; H, 7.91.

EXAMPLE 8

5-(α-D-glucopyranosyloxymethyl)-furan-2-carboxylic acid amide (formula 8)

300 mg (1.1 mmol) of the methyl ester of formula (7) were dissolved in a methanolic ammonia solution. After stirring for 24 h at room temperature the aminolysis was complete (TLC monitoring in acetonitrile/water (4:1). The solvent and excess ammonia were removed under vacuum and the white solid remaining was recrystallized by digestion with methanol/water: 270 mg (86%) of a crystalline powder, opalescent under the microscope, of m.p. 218° C. with $[α]_D^{20}=+97°$ (c=0.8, methanol).

$^1$H-NMR (300 MHz, DMSO-d$_6$): 3.07 (m, 1 H, 4'-H), 3.23 (m, 1 H, 2'-H), 3.35-3.61 (m, 4 H, 3'-H, 5'-H, 6'-H$_2$), 4.47 (d, 1 H, 7-H$_a$), 4.53 (t, 1 H, 6'-OH), 4.60 (d, 1 H, 7-H$_b$), 4.76 (m, 3 H, 1'-H, 2 OH), 4.89 (d, 1 H, OH), 6.57 (d, 1 H, 4-H), 7.07 (d, 1 H, 3-H), 7.37 (s, 1 H, NH), 7.74 (s, 1 H, NH); $J_{3,4}=3.3$, $J_{7a,7b}=13.2$, $J_{6',6'-OH}=5.7$ Hz.

MS (FD, 0-20 mA): m/e=303 (M+), 304 (M+ +1).

$C_{12}H_{17}NO_8$ (303.27): Calc. C, 47.53; H, 5.65; N, 4.62.
Found C, 47.57; H, 5.60; N, 4.51.

EXAMPLE 9

5-(α-D-glucopyranosyloxymethyl)-furan-2-carboxaldehyde oxime (formula 9)

To a solution of 3.1 g (10.7 mmol) glucosyloxymethylfurfural (formula 2, product of Example 1) in 50 ml ethanol was added a solution of 2.2 g (31.6 mmol) hydroxylammonium hydrochloride and 2.1 g (25 mmol) sodium acetate in 10 ml water and the mixture stirred for 10 min at room temperature. After this the thin-layer chromatogram (mobile solvent: water/n-propanol, 1:7) showed no further educt. To work up the product the solvent was removed under vacuum and the syrup remaining was taken up in 2-propanol. The precipitated salt was filtered off by suction. Further removal of the solvent gave a slightly coloured syrup which was further purified by adding to silica gel and eluting with chloroform/methanol (7:2). Evaporation of the eluate containing the GMF oxime (formula 9) and allowing the yellowish syrup to stand gave 2.3 g (71%) of colourless crystals of m.p. 138°-139° C.; $[α]_D^{20}=+118°$ (c=1.5, methanol).

$^1$H-NMR (300 MHz, D$_2$O): δ=3.4-3.8 (m, 5 H, 2'-H, 3'-H, 4'-H, 6'-H$_2$). 3.57 (ddd, 1 H, 5'-H), 4.7-4.9 (m, 2 H, 7-H$_2$), 5.04 (d, 1 H, 1'-H), 6.66 (d, 1 H, 4-H), 7.27 (d, 1 H, 3-H), 8.06 (s, 1 H, 6-H); $J_{3,4}=3.4$, $J_{1',2'}=3.6$, $J_{4',5'}=9.8$, $J_{5',6'a}=1.3$, $J_{5',6'b}=3.5$ Hz.

$^{13}$C-NMR (75.5 MHz, D$_2$O): δ=63.1, 64.3 (2 C, C-7, C-6'), 72.2 (C-4'), 74.0 (C-5'), 74.8 (C-2'), 75.8 (C-3'), 100.7 (C-1'), 115.3 (C-4), 121.8 (C-3), 140.4 (C-6), 147.9 (C-5), 155.2 (C-2).

MS (FD): m/e=303 (M+), 304 (M+ +1).

$C_{12}H_{17}NO_8$ (303.27): Calc. C, 47.53; H, 5.65; N, 4.62.
Found C, 47.48; H, 5.60; N, 4.64.

EXAMPLE 10

2-aminomethyl-5-(α-D-glucopyranosyloxymethyl)-furan (formula 10)

In a 125 ml stirred autoclave 5.76 g (0.02 mol) GMF was dissolved in 50 ml of methanol saturated with ammonia at 10° C. (ca. 5.5M) at 10° C. After the addition of 1 g alkaline Raney nickel, hydrogen was led in to a pressure of 100 atm and the mixture was heated to 60° C. The temperature was held constant for 1 h, and the mixture was then allowed to cool during a period of 4 h and filtered from catalyst after depressurising the reaction vessel. The filtrate was completely concentrated down under vacuum, resulting in a hard foam consisting of amine of the formula (10).

$^1$H-NMR (300 MHz, [D$_6$]-DMSO+D$_2$O): δ=3.10 (dd, 1 H, 4'-H), 3.19 (s, 2 H, 6-H$_2$), 3.24 (dd, 1 H, 2'-H), 3.45 (m, 2 H, 3'-H, 5'-H), 3.63 (m, 2 H, 6'-H$_2$), 4.38 (d, 1 H, 7-H$_a$), 4.52 (d, 1 H, 7-H$_b$), 4.77 (d, 1 H, 1'-H), 6.18 (d, 1 H, 4-H), 6.35 (d, 1 H, 3-H); $J_{3,4}=2.9$, $J_{7a,7b}=12.8$, $J_{1',2'}=3.5$, $J_{2',3'}=9.6$ Hz.

EXAMPLE 11

5-acetamidomethyl-2-(2',3',4',6'-tetra-O-acetyl-α-D-glucopyranosyloxymethyl)-furan (formula 11)

A solution of 0.9 g (2 mmol) of the nitrile of formula (14) in 50 ml ethyl acetate was hydrogenated in the presence of 100 mg 10% Pd on carbon at room temperature. After 12 h reaction was complete (TLC in methanol/chloroform, 2:1). After filtering off the catalyst and washing it with hot methanol (4×20 ml) the methanolic solution was treated with acetic anhydride (1.5 ml) and allowed to stand overnight. Removal of the methanol, digestion of the residue with ice water, extraction with chloroform, drying the combined extracts over magnesium sulfate, and removal of the solvent under vacuum gave 1.1 g (74%) of product of formula (11) as colourless crystals of m.p. 134°–135° C.: $[\alpha]_D^{20} = +121°$ (c=1.3, chloroform).

$C_{22}H_{29}NO_{12}$ (499.48): Calc. 52.90; H, 5.85; N 2.80. Found 52.93; H, 5.60; N 2.77.

The same product was also obtained in 87% yield by acetylation of the amine of formula (10) from Example 10 with pyridine/acetic anhydride.

EXAMPLE 12

5-(α-D-glucopyranosyloxymethyl)-furan-2-carbonitrile (formula 13)

A solution of 1.0 g (3.5 mmol) GMF of formula (2) in 30 ml DMSO was heated to 110° C. After addition of 310 mg (4.5 mmol) hydroxylammonium hydrochloride the temperature was maintained for a period of 30 min (TLC monitoring with 4:1 acetonitrile/water) and then rapidly lowered. The reaction mixture was concentrated under vacuum, the residue diluted with 30 ml water and extracted with dichloromethane (2×20 ml). The aqueous phase, after evaporation under vacuum, was purified by elution from a silica gel column (3×30 cm) with acetone. The fractions containing nitrile gave, on concentration, 0.6 g (61%) of nitrile of formula (13) as colourless needles of m.p. 113° C. and $[\alpha]_D^{20} = +119°$ C. (c=1, methanol).

$^1$H-NMR (300 MHz, [D$_6$]-DMSO): δ=3.04 (m, 1 H, 4'-H), 3.17 (m, 1 H, 2'-H), 3.27–3.58 (m, 4 H, 3'-H, 5'-H, 6'-H$_2$), 4.45 (t, 1 H, 6'-OH), 4.47 (d, 1 H, 7-H$_a$), 4.59 (d, 1 H, 7-H$_b$), 4.70 (d, 1 H, 1'-H), 4.77 (m, 2 H, OH), 4.87 (d, 1 H, OH), 6.54 (d, 1 H, 4-H), 7.51 (d, 1 H, 3-H); $J_{3,4}=3.6$, $J_{7a,7b}=13.5$, $J_{1',2'}=3.6$, $J_{6',6'-OH}=5.7$ Hz.

MS (FD): m/e=285 (M+), 286 (M+ +1).

$C_{12}H_{15}NO_7$ (285.25): Calc. C, 50.53; H, 5.30; N, 4.91. Found, C, 50.49; H, 5.32; N, 4.86.

EXAMPLE 13

5-(2',3',4',6'-tetra-O-acetyl-α-D-glucopyranosyloxymethyl)-furan-2-carbonitrile (formula 14)

A suspension of 3.0 g (10 mmol) GMF oxime (formula 9, product of Example 9) and 1.0 g freshly-melted sodium acetate in 10 ml acetic anhydride was stirred for 30 min at room temperature. The now clear solution was then made slightly acid with mineral acid by addition of hydrochloric acid (4 ml 4N HCl, 1.3 mole equiv. based on the sodium acetate used) and heated for a short time (5–8 min) to 60° C. Stirring into ice water, extraction with dichloromethane and evaporation of the combined extracts gave 3.5 g (78%) of the nitrile of formula (14) as a chromatographically homogenous syrup with $R_f=0.31$ (TCL in toluene/acetone, 4:1) and $[\alpha]_D^{20} = +135°$ (c=0.7, chloroform).

$^1$H-NMR (300 MHz, CDCl$_3$): δ=2.01, 2.04, 2.06, 2.10 (4 s, je 3 H, Ac-CH$_3$), 4.02–4.10 (m, 2 H, 5'-H, 6'-H$_a$), 4.27 (dd, 1 H, 6'-H$_b$), 4.59 (d, 1 H, 7-H$_a$), 4.69 (d, 1 H, 7-H$_b$), 4.86 (dd, 1 H, 2'-H), 5.08 (dd, 1 H, 4'-H), 5.18 (d, 1 H, 1'-H), 5.47 (dd, 1 H, 3'-H), 6.51 (d, 1 H, 4-H); $J_{3,4}=3.5$, $J_{7a,7b}=13.4$, $J_{1',2'}=3.8$, $J_{2',3'}=10.3$, $J_{3',4'}=9.7$, $J_{4',5'}=10.0$, $J_{5',6'}=4.5$, $J_{6'a,6'b}=12.5$ Hz.

—C-NMR (75.5 MHz, CDCl$_3$): δ=20.5, 20.6, 20.7 (4 C, Ac-CH$_3$), 61.5, 61.8 (2 C, C-7, C-6'), 67.9, 68.5, 69.8, 70.7 (4 C, C-2', C-3',C-4', C-5'), 95.3 (C-1'), 111.1 (C-5), 111.2 (C-4), 122.7 (C-3), 125.6 (C-2), 155.7 (C-6), 169.5, 169.9, 170.1, 170.5 (4 C, Ac-CO).

MS (FD): m/e=453 (M+), 454 (M+ +1).

$C_{20}H_{23}NO_{11}$ (453.41) Calc. C, 52.98; H, 5.11; N, 3.09. Found. C, 52.99; H, 4.87; N, 3.06.

EXAMPLE 14

2-(benzoylvinyl)-5-(glucopyranosyloxymethyl)-furan (formula 15)

A solution of 4.5 g GMF (15 mmol) and 1.8 g (15 mmol) acetophenone on 50 ml ethanol was cooled to 0° C. and 15 ml of 10% NaOH was added dropwise to it with stirring. After 30 min it was diluted with 50 ml water, extracted with dichloromethane (3×60 ml), the combined extracts were washed neutral with saturated potassium hydrogen sulfate solution and a little water and dried (MgSO$_4$). On concentration of the solution crystallisation occurred: 4.1 g (70%) light yellow crystals of m.p. 127° C.; $[\alpha]_D^{20} = +111°$ (c=0.9, methanol).

$^1$H-NMR (300 MHz, CDCl$_3$): δ=3.48–3.78 (m, 7 H, 2'-H, 3'-H, 4'-H, 5'-H, 6'-H$_2$, OH), 4.10 (d, 1 H, OH), 4.50 (d, 1 H, 9-H$_a$), 4.57 (d, 1 H, 9-H$_b$), 4.75 (s, 1-H, OH), 4.92 (d, 1 H, 1'-H), 4.98 (s, 1 H, OH), 6.39 (d, 1 H, 4H), 6.56 (d, 1 H, 3H), 7.28–7.52 (m, 5 H, COC$_6$H$_5$), 7.93 (d, 2 H, 6-H, 7-H); $J_{3,4}=3.3$, $J_{9a,9b}=13.5$, $J_{1',2'}=3.2$ Hz.

$^{13}$C-NMR (75.5 MHz, DMSO-d$_6$): δ=60.2 (C-9), 60.8 (C-6'), 70.1 (C-4'), 71.4 (C-2'), 73.1 (C-3', C-5'), 98.0 (C-1'), 112.4 (C-4), 118.0 (C-3), 118.5, 128.2, 130.4, 133.0 und 137.4 (C$_6$H$_5$), 128.8 (C-6, C-7), 151.0 (C-5), 154.8 (C-2), 188.5 (C=0).

MS (FD): m/e=390 (M+).

$C_{20}H_{22}O_8$ (390.38): Calc. C, 61.53; H, 5.68. Found. C, 61.49; H, 5.65.

EXAMPLE 15

2-(dicyanovinyl)-5-(α-D-glucopyranosyloxymethyl)-furan (formula 16)

1 g (3.5 mmol) GMF of formula (1) and 230 mg (3.5 mmol) malonic acid dinitrile were dissolved in 10 ml methanol and 600 mg alumininium oxide (dried at 120° C. for 24 h) were added thereto. After stirring for 3 h at room temperature (TLC monitoring with acetonitrile/water, (4:1)) the catalyst was filtered off and the solvent removed under vacuum. After purification of the crude product by elution from a silica gel column (3×20 cm) with acetone, 780 mg (66%) of product of the formula (16) crystallized on evaporation of the solvent in the form of light yellow needles of m.p. 138° C. and $[\alpha]_D^{20} = +104°$ (c=0.6, methanol).

$^1$H-NMR (300 MHz, D$_2$O): δ=3.44 (dd, 1 H, 4'-H), 3.58 (dd, 1 H, 2'-H), 3.68—3.76 (m, 4 H, 3'-H, 5'-H, 6'-Hz), 4.77 (d, 1 H, 7$_a$-H), 4.84 (d, 1 H, 7$_b$-H), 5.09 (d, 1 H, 1'-H), 6.83 (d, 1 H, 4-H), 7.39 (d, 1 H, 3-H), 7.91 (s, 1 H, 6-H); $J_{3,4}=3.7$, $J_{7a,7b}=13.5$, $J_{1',2'}=3.7$, $J_{2',3'}=9.8$ Hz.

IR (KBr): ν=2240 cm⁻¹ (C≡N).
MS (FD, 10 mA): m/e=336 (M+).
C₁₅H₁₇NO₉ (336.30): Calc. C, 53.57; H, 4.80; N, 8.33,
Found, C, 53.42; H, 4.83; N, 8.25.

What is claimed is:

1. A process for the production of 5-(α-D-glucopyranosyloxy-methyl)-furan-2-carboxaldehyde which comprises dissolving a compound selected from the group consisting of anhydrous isomaltulose and isomaltulose monohydrate in a strongly polar aprotic solvent in the proportion of from 10 to 100 g of isomaltulose to 100 g of solvent and contacting the solution at a temperature of from 70° to 150° C. with an acid ion-exchanger in the H+ form as a catalyst, wherein when the process is carried out batchwise the ratio of isomaltulose to ion-exchanger is from 20:1 to 10:1 and the duration of contact is from 0.1 to 24 hours and when the process is carried out continuously the solution is percolated through a column of the ion-exchanger so that the contact time is from 20 seconds to 60 minutes, and further comprising recovering the 5-(α-D-glucopyranosyloxymethyl)-furan-2-carboxaldehyde from the aprotic solvent.

2. A process for the production of O-acyl derivatives of 5-(α-D-glucopyranosyloxymethyl)-furan-2-carboxaldehyde which comprises reacting said 5-(α-D-glucopyranosyloxymethyl)-furan-2-carboxaldehyde with an acylating agent selected from the group consisting of acetic anhydride, acetyl chloride and benzoyl chloride in an anhydrous organic solvent.

3. A process for the production of alcohol derivatives of 5-(α-D-glucopyranosyloxymethyl)-furan-2-carboxaldehyde and O-acyl derivatives thereof which comprises reduction of said 5-(α-D-glucopyranosyloxymethyl)-furan-2-carboxaldehyde or O-acyl derivative thereof with a reducing agent selected from the group consisting of alkali metal borohydride, aluminum hydride and trialkylsilane.

4. A compound derived from 5-(α-D-glucopyranosyloxymethyl)-furan-2-carboxaldehyde selected from the group consisting of compounds of the general formula (I):

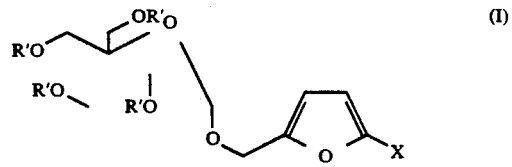

wherein R' is one of a hydrogen atom, a lower alkyl or benzyl acyl group and a lower alkyl group and X represents one of —CH₂OH, —COOH, —C(H)=NOH, —CN, —CH₂NHR" and —CH=CR"R''', wherein R" is one of a hydrogen atom, a lower acyl group, an aryl group and an alkyl group with up to 20 C atoms and R''' is one of a hydrogen atom, —NO₂, —CN, —COOalkyl and benzoyl.

5. A compound according to claim 4, which is 2-(α-D-glucopyranosyloxymethyl)-5-hydroxymethyl furan.

6. A compound according to claim 4, which is the oxime of 5-(α-D-glucopyranosyloxymethyl)-furan-2-carboxaldehyde.

7. A compound according to claim 4, which is 5-(α-D-glucopyranosyloxymethyl)-furan-2-carboxylic acid.

8. A compound according to claim 4, which is 5-(2',3',4',6'-tetra-O-acetyl-α-D-glucopyranosyloxymethyl)-furan-2-carbonitrile.

9. A compound according to claim 4, which is 5-acetamidomethyl-2(2',3',4',6'-tetra-O-acetyl-α-D-glucopyranosyloxy-methyl)-furan.

10. A compound according to claim 4, which is 2-(benzoylvinyl)-5-(glucopyranosyloxymethyl)-furan.

11. A compound according to claim 4, which is 2-(dicyanovinyl)-5-(α-D-glucopyranosyloxymethyl)-furan.

12. A process for the production of carboxylic acids from 5-(α-D-glucopyranosyloxymethyl)-furan-2-carboxaldehyde and O-acyl derivatives thereof comprising reacting said 5-(α-D-glucopyranosyloxymethyl)-furan-2-carboxaldehyde or O-acyl derivatives with an oxidizing agent selected from the group consisting of sodium chlorite, sodium bichromate and bromine water.

13. A process for the production of oximes from 5-(α-D-glucopyranosyloxymethyl)-furan-2-carboxaldehyde and O-acyl derivatives thereof comprising reaction of said 5-(α-D-glucopyranosyloxymethyl)-furan-2-carboxaldehyde or O-acyl derivatives with hydroxylamine.

* * * * *